(12) United States Patent
Banavali et al.

(10) Patent No.: US 8,329,949 B2
(45) Date of Patent: Dec. 11, 2012

(54) PREPARATION OF NITRONES

(75) Inventors: Rajiv Manohar Banavali, Rydal, PA (US); Bharati Dinkar Chheda, Houston, TX (US); Barry Weinstein, Dresher, PA (US)

(73) Assignee: Rohm and Haas Company, Philadelphia, PA (US)

( * ) Notice: Subject to any disclaimer, the term of this patent is extended or adjusted under 35 U.S.C. 154(b) by 1018 days.

(21) Appl. No.: 12/291,744

(22) Filed: Nov. 12, 2008

(65) Prior Publication Data

US 2009/0126263 A1  May 21, 2009

Related U.S. Application Data

(60) Provisional application No. 61/003,177, filed on Nov. 15, 2007, provisional application No. 61/069,450, filed on Mar. 14, 2008.

(51) Int. Cl.
 *C07C 249/00* (2006.01)
 *C10L 1/228* (2006.01)
 *C10L 1/23* (2006.01)
(52) U.S. Cl. .................................. 564/248; 44/420
(58) Field of Classification Search .......... 514/490; 564/248; 44/420
See application file for complete search history.

(56) References Cited

U.S. PATENT DOCUMENTS

| | | | |
|---|---|---|---|
| 5,455,272 A | 10/1995 | Janzen et al. | |
| 5,527,828 A | 6/1996 | Janzen et al. | |
| 5,532,277 A | 7/1996 | Janzen et al. | |
| 6,512,143 B1 | 1/2003 | Blixt | |
| 6,762,322 B1 | 7/2004 | Parker | |
| 2002/0165274 A1* | 11/2002 | Waterbury et al. | 514/490 |
| 2005/0182060 A1 | 8/2005 | Kelly et al. | |

OTHER PUBLICATIONS

Christensen, et al, "Oxidation of Imines to Nitrones by the Permanganate Ion", J. Org. Chem, vol. 54, pp. 126-131 (1989).
Boyd, et al., "Imines and Derivatives. Part 24.1 Nitrone Synthesis by Imine Oxidation Using Either a Peroxyacid or . . . " J. Chem Soc. Perkin Trans. I, pp. 301-306, (1990).
Koshelev, et al., "Stabilization of Ecologically Pure Diesel Fuel With Composition Additives," J. Khimiya I Tekhnologiya Topliv I Masel, vol. 4, pp. 29-31 (1996).

* cited by examiner

*Primary Examiner* — Ellen McAvoy
*Assistant Examiner* — Chantel Graham
(74) *Attorney, Agent, or Firm* — Kenneth Crimaldi

(57) ABSTRACT

A method for producing a nitrone of formula (I)

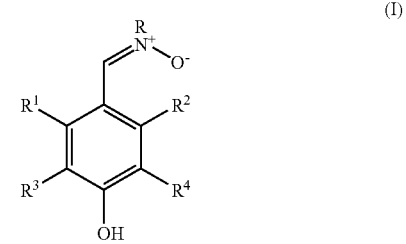

(I)

wherein R is a branched alkyl group having from four to thirty carbon atoms; $R^1$, $R^2$, $R^3$ and $R^4$ independently are hydrogen or alkyl groups having from one to six carbon atoms from an imine having formula (II)

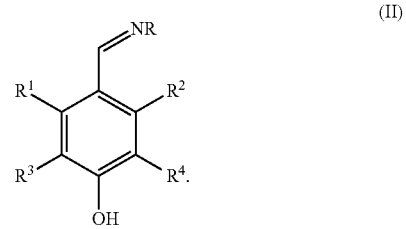

(II)

4 Claims, No Drawings

PREPARATION OF NITRONES

This is a non-provisional application of prior pending U.S. Provisional Application Ser. No. 61/003,177 filed on Nov. 15, 2007 and U.S. Provisional Application Ser. No. 61/069,450 filed on Mar. 14, 2008.

This invention relates to a method for preparation of aromatic nitrone compounds, and to a method for use of the nitrone compounds as fuel and oil stabilizers.

Nitrones have been prepared by a variety of methods. For example, U.S. Pat. No. 5,527,828 discloses aromatic nitrones produced by condensation of alkylhydroxylamines with benzaldehydes. However, most alkylhydroxylamines are not available commercially, and must be synthesized in a separate step.

The problem addressed by this invention is to find an alternative preparation of nitrones.

STATEMENT OF INVENTION

The present invention provides a method for producing a nitrone of formula (I)

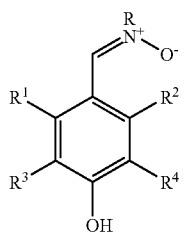

(I)

wherein R is a branched alkyl group having from four to thirty carbon atoms; $R^1$, $R^2$, $R^3$ and $R^4$ independently are hydrogen or alkyl groups having from one to six carbon atoms; said method comprising treating an imine having formula (II)

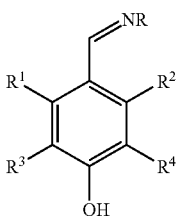

(II)

with a peroxy acid.

The present invention further provides a method for stabilizing fuel or lubricating oil by adding 0.01 to 5 wt % of the nitrone of formula (I).

The present invention further provides novel compounds of formula (I) in which R is tertiary and has from nine to thirty carbon atoms.

DETAILED DESCRIPTION

Percentages are weight percentages ("wt %") and temperatures are in ° C.; unless specified otherwise. An "alkyl" group is a saturated hydrocarbyl group having from one to thirty carbon atoms in a linear, branched or cyclic arrangement. A "peroxy acid" is an organic compound having a peroxy carboxylic acid group, C(O)OOH. Preferably, a peroxy acid is an aromatic peroxy acid, more preferably peroxybenzoic acid or a substituted (e.g., alkyl, nitro, alkoxy, halo) peroxybenzoic acid, and most preferably meta-chloroperoxybenzoic acid ("MCPBA"). A "fuel" is any substance burned in an internal combustion engine or heating furnace, including, e.g., gasoline, kerosene, diesel fuel, jet fuel, biodiesel fuel, fuel oil, and bunker C fuel (number 6 fuel oil for marine applications).

The imine of formula (II) may be prepared and isolated prior to treatment with peroxy acid, or the imine may be formed and treated with peroxy acid without isolation. The imine typically is prepared from 3,5,-di-tert-butyl-4-hydroxybenzaldehyde and an amine $RNH_2$, although other preparations of imines are known in the art.

In some embodiments of the invention, the branched alkyl group R is a tertiary alkyl group. In some embodiments, the tertiary alkyl group is derived from one or more of the PRIMENE™ amines available from Rohm and Haas Company; Philadelphia, Pa. For example, an isomeric mixture of $C_{16}$ to $C_{22}$ tertiary alkyl primary amines (PRIMENE JM-T amine); an isomeric mixture of $C_8$ to $C_{10}$ tertiary alkyl primary amines (PRIMENE BC-9 amine); an isomeric mixture of $C_{10}$ to $C_{15}$ tertiary alkyl primary amines (PRIMENE 81-R amine); or mixtures thereof. In some embodiments, the amine is a diamine in which each amino group is attached to a tertiary alkyl group. An example of such an amine is PRIMENE MD amine, available from Rohm and Haas Company; Philadelphia, Pa. In these embodiments, preferably the PRIMENE amine is condensed with the corresponding substituted benzaldehyde to produce imine (II).

In some embodiments of the invention, the branched alkyl group R is derived from a cyclic or polycyclic amine having from six to twenty carbon atoms, alternatively from eight to sixteen carbon atoms. In some embodiments, R is tertiary alkyl. Examples of suitable cyclic or polycyclic amines include 1-aminoadamantane and PRIMENE MD amine.

In some embodiments of the invention, the branched alkyl group R has at least six carbon atoms, alternatively at least eight carbon atoms. In some embodiments, the branched alkyl group R is tertiary, and has from eight to twenty-two carbon atoms, alternatively from eight to sixteen carbon atoms, although small amounts, i.e., less than 1% of larger alkyl groups are permitted in either case. For example, PRIMENE amines contain small amounts of larger alkyl groups.

In some embodiments of the invention, $R^1$, $R^2$, $R^3$ and $R^4$ are alkyl groups having from one to four carbon atoms. In some aspects of these embodiments, $R^3$ and $R^4$ are alkyl groups having from one to four carbon atoms and $R^1$ and $R^2$ are hydrogen or methyl; alternatively, $R^3$ and $R^4$ are alkyl groups having from one to four carbon atoms and $R^1$ and $R^2$ are hydrogen; alternatively, $R^3$ and $R^4$ are tert-butyl and $R^1$ and $R^2$ are hydrogen or methyl; alternatively $R^3$ and $R^4$ are tert-butyl and $R^1$ and $R^2$ are hydrogen. A particularly preferred nitrone has formula (III):

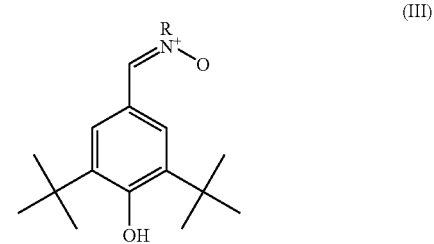

(III)

In some embodiments of the invention, the nitrone is prepared from the corresponding substituted benzaldehyde, e.g., 3,5-di-tert-butyl-4-hydroxybenzaldehyde, without isolation of the imine. In these embodiments, the benzaldehyde and the amine, $RNH_2$ are contacted, and water is removed, preferably by distillation or by use of a dehydrating agent. Peroxy acid is then combined with the resulting imine solution.

In some embodiments of the invention, the imine is combined with the peroxy acid at a temperature from −30° C. to 20° C., In some embodiments, the temperature is no more than 15° C., alternatively no more than 10° C., alternatively no more than 5° C. In some embodiments, the temperature is at least −20° C., alternatively at least −10° C. Preferably, the reaction mixture is kept in this temperature range for at least 30 minutes after the imine and peroxy acid are combined, alternatively at least 60 minutes, alternatively at least 2 hours. After this time, the temperature of the reaction mixture typically is raised to at least 10° C., alternatively at least 15° C.; but no more than 30° C., alternatively no more than 25° C. Preferably, the reaction mixture is maintained in this higher temperature range for at least 1 hour, alternatively at least 2 hours, alternatively at least 4 hours.

The solvent for the reaction may be any solvent in which the imine and the peroxy acid are soluble, and which does not react significantly with the peroxy acid. For example, suitable solvents include methylene chloride, ethyl acetate, methyl acetate, t-butanol, diethyl ether, ethanol and chloroform. Ethyl acetate is preferred.

In embodiments of the invention in which the nitrone of formula (I) is added to lubricating oil or fuel as a stabilizer, preferably the amount of nitrone added is at least 0.001%, alternatively at least 0.01%, alternatively at least 0.05 wt %, alternatively at least 0.1 wt %, alternatively at least 0.2 wt %. Preferably, the amount of nitrone is no greater than 3 wt %, alternatively no greater than 2 wt %, alternatively no greater than 1 wt %, alternatively no greater than 0.5 wt %. Other additives that could be used in combination with the nitrone of formula (I) include ZDDP (zinc dithio dialkyl phosphates), octylated or butylated diphenylamines, and hindered phenols.

EXAMPLES

Example 1

Preparation of 2,6-di-tert-butyl-4-(N-tert-octyl) nitronyl phenol (DBONP) With Isolation of Imine (a) Preparation of 2,6-di-tert-butyl-4-((2,4,4-trimethylpentan-2-ylimino)methyl)phenol To a nitrogen-charged 250 mL, 4-necked round bottom flask equipped with a TEFLON-coated magnetic stirrer, a thermometer, nitrogen gas flow, addition funnel, and a Dean-Stark apparatus equipped with a condenser and a receiver was added 9.8590 g (0.042 moles) of 3,5,-di-t-butyl-4-hydroxybenzaldehyde followed by 100 mL of toluene with vigorous stirring. The solution was not clear and the aldehyde was not soluble in toluene at room temperature. 5.8 gm of t-octylamine was added into the reaction via addition funnel. The reaction flask was slowly heated to 60° C. by heating mantle, and the temperature was controlled by a THERM-O-WATCH® Controller/Monitor. The solution became clear dark reddish brown. The reaction was monitored for 2 hours at 60° C. by Thin Layer Chromatography (TLC). Then the temperature was raised to 110° C. to remove the water by azeotrope with toluene. The azeotrope of water and toluene was collected in a receiver attached to Dean-Stark. After the calculated amount of water was removed, the reaction was cooled to room temperature. The completion of the reaction was monitored by Infra Red Spectroscopy (IR) analysis and by the amount of water collected in the Dean-Stark receiver. The IR analysis confirmed the disappearance of wave number 1682 $cm^{-1}$ (aldehyde C=O) and appearance of wave number 1621 $cm^{-1}$ (imine C=N). The imine was collected by evaporating toluene using a rotary evaporator under water aspiration with 94.48% yield.

(b) Preparation of 2,6-di-tert-butyl-4-(N-tert-octyl) nitronyl phenol (DBONP)

13.7 g of (0.0396 moles) of 2,6-di-tert-butyl-4-((2,4,4-trimethylpentan-2-ylimino)methyl)phenol from part (a) was added to a 500 mL 3-neck round bottom flask equipped with a thermometer, a condenser, and an addition feed funnel with pressure-equalization arm. 100 mL methylene chloride was added in to the flask to dissolve the imine. A solution of 10.18 g of purified meta-chloroperoxybenzoic acid (commercially available MCPBA typically is 70 to 77% pure. The impurity is m-chlorobenzoic acid, which is more acidic than the peracid. MCPBA is thus purified by washing with a phosphate buffer of pH 7.5 and drying at reduced pressure.) in 100 mL of ethyl acetate was made in a beaker and transferred in to the feed funnel. The reaction flask was cooled to 0° C. using ice bath. Once the temperature reached 0° C., the solution of MCPBA from the feed funnel was fed in to the reaction flask slowly over a 45 to 60 minute period, while maintaining the temperature at 0° C. The reaction mixture turned initially bluish in color and eventually changed to green. The reaction mixture was held for 2 hours at 0° C. and then slowly allowed to warm to room temperature. The reaction mixture was transferred to a 1-liter separatory funnel. The mixture was then washed twice with 100 mL of 7% $NaHCO_3$ solution followed by water wash 2×100 mL each. Then the mixture was washed twice with 100 mL of saturated sodium chloride solution, then with 2×100 mL water. The mixture was then dried overnight using $Na_2SO_4$ or $MgSO_4$. The crude nitrone then was concentrated using a rotary evaporator. The nitrone is purified using flash chromatography column using silica gel (66 A°), and product eluted with mixture of hexane/ethyl acetate ("EtOAc") (70:30) to give 13.56 gm of yellowish color solid crystals. The final product was recrystallized with pentane to give 12.1 gm of off-white crystalline solids. The melting point was 150-155° C.

Example 2

Preparation of (DBONP) Without Isolation of Imine

To a nitrogen charged 250 mL, 4-necked round bottom flask equipped with a Teflon coated magnetic stirrer, a thermometer, nitrogen gas flow, addition funnel, and a Dean-Stark apparatus equipped with a condenser and a receiver was added 9.8590 gm (0.042 moles) of 3,5,-di-t-butyl-4-hydroxybenzaldehyde followed by 100 mL of toluene with vigorous stirring. The solution was not clear and the aldehyde was not soluble in toluene at room temperature. 5.8 gm of t-octylamine was added into the reaction via addition funnel. The reaction flask was slowly heated to 60° C. by heating mantle, and the temperature was controlled by a THERM-O-WATCH® Controller/Monitor. The solution became clear dark reddish brown. The reaction was monitored for 2 hours at 60° C. by Thin Layer Chromatography (TLC). Then the temperature was raised to 110° C. to remove the water by azeotrope with toluene. The azeotrope of water and toluene was collected in a receiver attached to a Dean-Stark apparatus. After the calculated amount of water was removed, the reaction was cooled to room temperature. The completion of the reaction was monitored by Infra Red Spectroscopy (IR) analysis and by the amount of water collected in the Dean-Stark receiver. The IR analysis confirmed the disappearance of wave number 1682 cm$^{-1}$ (aldehyde C=O) and appearance of wave number 1621 cm$^{-1}$ (imine C=N). The Dean-Stark apparatus, the condenser, and the receiver were removed. An addition funnel with pressure-equalization arm was attached to the reaction flask. A solution of 10.18 gm of purified MCPBA in 100 mL of ethyl acetate was made in a beaker and transferred in to the addition funnel. The reaction flask was cooled to 0° C. using ice bath. Once the temperature reached 0° C., the solution of MCPBA from the feed funnel was fed in to the reaction flask slowly over a 45 to 60 minute period, while maintaining the temperature at 0° C. The reaction mixture turned initially milky bluish color and eventually changed to milky green. The reaction mixture was held for 2 hours at 0° C. and then slowly allowed to warm to room temperature. The reaction mixture turned clear green at room temperature. The reaction mixture was stirred for an additional 2 to 8 hr at room temperature. The reaction mixture was transferred to a 1-liter separatory funnel. The mixture was then washed twice with 100 mL of 7% NaHCO$_3$ solution, then with 2×100 mL water. Then the mixture was washed twice with 100 mL of saturated sodium chloride solution followed by wash with 2×100 mL water. The mixture was then dried over Na$_2$SO$_4$ or MgSO$_4$. The crude nitrone then was concentrated using a rotary evaporator. Analysis of the crude nitrone by $^1$H NMR did not detect any oxaziridine byproduct. The nitrone was purified using flash chromatography column using silica gel (66 A°), and product eluted with mixture of hexane/EtOAc (70:30) to give 13.56 gm of yellowish color solid crystals. The final product was recrystallized with pentane to give 12.1 gm of off-white crystalline solids. The melting point was 150-155° C. Anti-oxidancy properties were evaluated by ESR technique and compared with PBN (phenyl t-butyl nitrone). The data showed that the nitrone made from tert-octylamine and 3,5-di-t-butyl-4-hydroxy benzaldehyde (Ex. 2) and the nitrone made from tert-butylamine and 3,5-di-t-butyl-4-hydroxy benzaldehyde (Ex. 3) showed better efficiency compared to PBN as shown in Table 1 below:

TABLE 1

| Nitrone | Rate constant, k | Regression coefficient | Concentration, c | Comparison with PBN |
|---|---|---|---|---|
| PBN | 4.47 * 10$^9$ M$^{-1}$ * s$^{-1}$ | 0.8624 | <0.07 mM | 1 |
| Ex. 2 | 9.79 * 10$^9$ M$^{-1}$ * s$^{-1}$ | 0.944 | 0.005-0.05 mM | 2.19 |
| Ex. 3 | 7.65 * 10$^9$ M$^{-1}$ * s$^{-1}$ | 0.8667 | 0.005-0.05 mM | 1.71 |

The above data clearly indicate that the nitrone made from t-octylamine and 3,5-di-t-butyl-4-hydroxybenzaldehyde following the synthesis route mentioned above, is better compared to PBN in terms of scavenging hydroxyl radical.

Two additional nitrones were made using the procedure of Example 2, with PRIMENE 81-R amine (Ex. 4) or PRIMENE JM-T amine (Ex. 5). These nitrones, along with the one of Ex. 2 and PBN, were tested in base oil for antioxidancy according to ASTM procedure E 2009. The results for oxidation onset temperature ("OOT") are presented below in Table 2.

TABLE 2

| Nitrone | % in oil | OOT (° C.) |
|---|---|---|
| none | 0 | 195 |
| PBN | 0.5 | 197 |
| Ex. 2 | 0.5 | 227 |
| Ex. 4 | 0.5 | 220 |
| Ex. 5 | 0.5 | 203 |
| PBN | 0.25 | 196.5 |
| Ex. 2 | 0.25 | 223 |
| Ex. 4 | 0.25 | 216.4 |
| Ex. 5 | 0.25 | 204.5 |

Nitrones from Ex 2, 4, and 5 along with PBN and antioxidant (mixture of Mono-, Di-, and Tri-tert-butylphenol) were tested in B-100 biodiesel fuel (100% biodiesel fuel, ASTM D 6751) for antioxidancy according to the European EN 14112 test procedure. The results for induction period in hours (h) at 110° C. are presented in Table 3.

TABLE 3

| Nitrone | % in B-100 | Induction Period @ 110° C. (h) |
|---|---|---|
| none | 0 | 1.93 |
| mixture of Mono-, Di-, and Tri-tert-butylphenol | 0.01 | 9.57 |
| Ex 2 | 0.01 | >17 |
| Ex 4 | 0.01 | 12.15 |
| Ex 5 | 0.01 | 8.53 |
| PBN | 0.01 | 0.9 |
| mixture of Mono-, Di-, and Tri-tert-butylphenol | 0.005 | 6.81 |
| Ex 2 | 0.005 | 9.1 |
| Ex 4 | 0.0042 | 7.96 |
| Ex 5 | 0.0042 | 6.8 |
| PBN | 0.005 | 2.02 |

The invention claimed is:
1. A compound of formula (I)

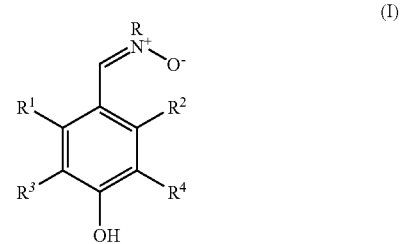

wherein R is a tertiary alkyl group having from ten to twenty-two carbon atoms; and R$^1$, R$^2$, R$^3$ and R$^4$ independently are hydrogen or alkyl groups having from one to four carbon atoms.

2. The compound of claim 1 in which R$^3$ and R$^4$ are tert-butyl; and R$^1$ and R$^2$ are hydrogen.

3. The compound of claim 2 in which R has from ten to fifteen carbon atoms.

4. The compound of claim 2 in which R has from sixteen to twenty-two carbon atoms.

* * * * *